US012672780B2

(12) United States Patent

Mikami et al.

(10) Patent No.: US 12,672,780 B2

(45) Date of Patent: Jul. 7, 2026

(54) PALPATION SUPPORT DEVICE AND PALPATION SUPPORT METHOD

(71) Applicant: Canon Kabushiki Kaisha, Tokyo (JP)

(72) Inventors: Seiji Mikami, Otawara (JP); Shingo Takagi, Otawara (JP); Kei Yamaji, Nasushiobara (JP); Seito Igarashi, Nasushiobara (JP); Norimasa Muroi, Nasushiobara (JP); Hiroshi Kurosawa, Nasushiobara (JP); Satoshi Okuyama, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 949 days.

(21) Appl. No.: 17/592,863

(22) Filed: Feb. 4, 2022

(65) Prior Publication Data

US 2022/0240781 A1 Aug. 4, 2022

(30) Foreign Application Priority Data

Feb. 4, 2021 (JP) ................................. 2021-016767

(51) Int. Cl.
*A61B 5/00* (2006.01)

(52) U.S. Cl.
CPC .......... *A61B 5/0053* (2013.01); *A61B 5/4803* (2013.01); *A61B 5/4824* (2013.01); *A61B 5/6826* (2013.01)

(58) Field of Classification Search
CPC ... A61B 5/0053; A61B 5/4803; A61B 5/4824; A61B 5/6826; A61B 5/48; A61B 5/00; A61B 5/0048
See application file for complete search history.

(56) References Cited

U.S. PATENT DOCUMENTS

| | | | |
|---|---|---|---|
| 6,491,649 B1 | 12/2002 | Ombrellaro | |
| 6,726,638 B2 | 4/2004 | Ombrellaro | |
| 2011/0144541 A1 | 6/2011 | Kuroda et al. | |
| 2013/0172776 A1* | 7/2013 | Gaw .................... | A61B 5/4878 |
| | | | 600/547 |
| 2016/0345899 A1* | 12/2016 | Mi ......................... | A61B 5/064 |
| 2018/0315504 A1* | 11/2018 | Inada ................... | A61B 5/0053 |

FOREIGN PATENT DOCUMENTS

| | | |
|---|---|---|
| JP | 11-48166 A | 2/1999 |
| JP | 2001-100879 A | 4/2001 |
| JP | 2003-209821 A | 7/2003 |
| JP | 2003-271737 A | 9/2003 |

(Continued)

OTHER PUBLICATIONS

Japanese Office Action issued Jun. 14, 2024 in Japanese Patent Application No. 2021-016767, 2 pages.

(Continued)

*Primary Examiner* — Tse W Chen
*Assistant Examiner* — Evelyn Grace Park
(74) *Attorney, Agent, or Firm* — Oblon, McClelland, Maier & Neustadt, L.L.P.

(57) ABSTRACT

A palpation support device according to an embodiment includes: a palpation data acquiring part configured to acquire a palpation data based on a plurality of pressure values applied to fingers of an examiner; and a diagnosis support information output part configured to output diagnosis support information based on the palpation data.

11 Claims, 17 Drawing Sheets

(56)     References Cited

FOREIGN PATENT DOCUMENTS

| JP | 2004-510479 | A | 4/2004 |
| JP | 2005-192577 | A | 7/2005 |
| JP | 2006-502818 | A | 1/2006 |
| JP | 2011-120727 | A | 6/2011 |

OTHER PUBLICATIONS

Office Action issued Jun. 18, 2025, in corresponding Chinese Patent Application No. 202210078030.9, 7 pages.
Office Action issued Jan. 21, 2026, in corresponding Chinese Patent Application No. 202210078030.9 with English translation, 12 pages.
Office Action issued Apr. 20, 2026, in corresponding Chinese Patent Application No. 202210078030.9, 5 pages.

* cited by examiner

INFORMATION PROCESSING
DEVICE FOR DOCTOR

INFORMATION PROCESSING
DEVICE FOR PATIENT

DISPLAY PORTION
FOR DIAGNOSIS          S11

GENERATE OBSERVATION
POSITION DATA          S12

SPECIFY PORTION
FOR DIAGNOSIS          S13

GENERATE EXAMINATION
POSITION DATA          S14

STORE DATA          S16

TRANSMIT DATA          S15

| PORTION | POSITION COORDINATE SYSTEM ON PATIENT SIDE (x, y, z) | POSITION COORDINATE SYSTEM ON DOCTOR SIDE (a, b, c) |
|---|---|---|
| HEAD | 0,0,0 | 0,0,0 |
| NECK | 30,0,8 | 0,20,5 |
| SHOULDER | 45,0,8 | 0,30,6 |
| ABDOMEN | 70,0,8 | 0,50,6 |
| TOE | 175,0,0 | 0,120,-10 |

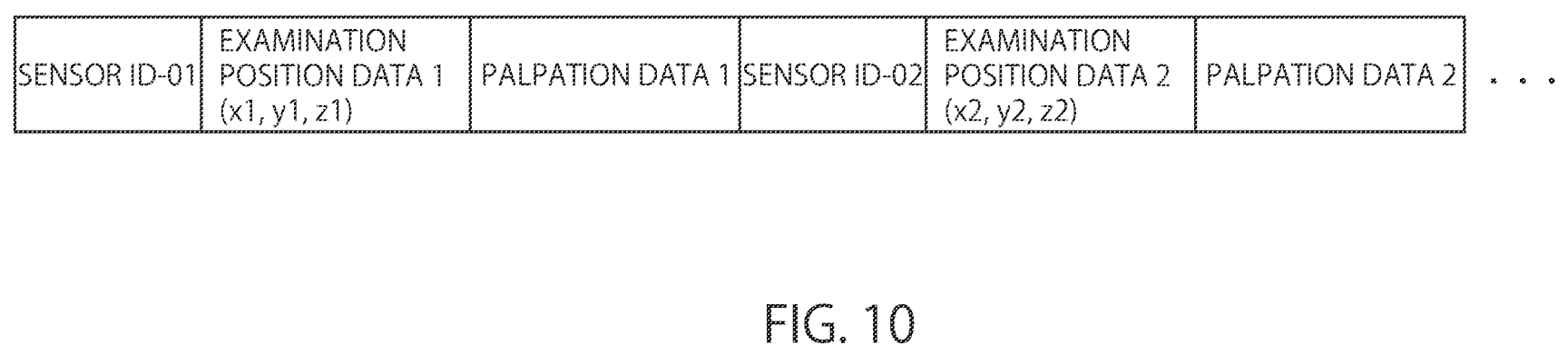

| SENSOR ID-01 | EXAMINATION POSITION DATA 1 (x1, y1, z1) | PALPATION DATA 1 | SENSOR ID-02 | EXAMINATION POSITION DATA 2 (x2, y2, z2) | PALPATION DATA 2 | ... |

FIG. 10

PALPATION SUPPORT DEVICE AND PALPATION SUPPORT METHOD

CROSS REFERENCE TO RELATED APPLICATIONS

This application is based upon and claims the benefit of priority from the prior Japanese Patent Application No. 2021-016767, filed on Feb. 4, 2021, the entire contents of which are incorporated herein by reference.

FIELD

The embodiments described herein and illustrated in the accompanying drawings relate to a palpation support device and a palpation support method.

BACKGROUND

As the population of older people increases or in order to prevent infection with new viruses, the demand for online diagnosis services is increasing. In order to conduct online diagnosis, sometimes remote palpation may be required to find illness caused by a tumor, for example. During remote palpation, a doctor may receive palpation data indicating the pressure applied to a portion that needs a diagnosis of a patient, and make a diagnosis based on the palpation data.

However, the doctor cannot obtain the palpation data by directly touching the patient. Therefore, the doctor may not be sure whether the palpation data is obtained by a palpation method that the doctor considers necessary. This may make the data unreliable.

BRIEF DESCRIPTION OF THE DRAWINGS

FIG. 10 illustrates an example of a configuration of transmitted data.

DETAILED DESCRIPTION

A palpation support device according to an embodiment includes:

a palpation data acquiring part configured to acquire palpation data based on a plurality of pressure values applied to fingers of an examiner; and a diagnosis support information output part configured to output diagnosis support information based on the palpation data.

Embodiments will now be described with reference to the accompanying drawings. It should be noted that the present invention is not limited to the embodiments described below.

First Embodiment

Figure 1:
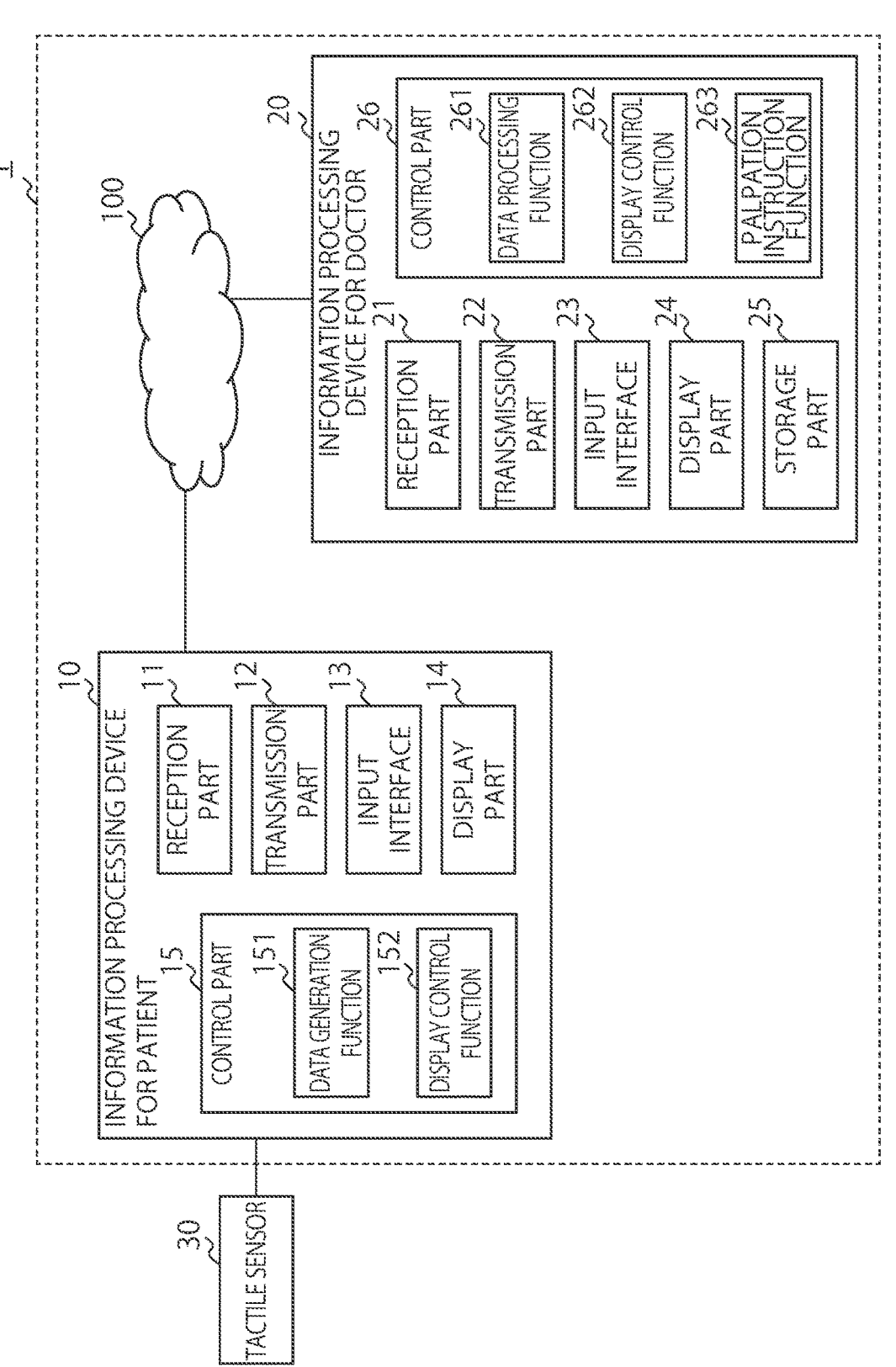
FIG. 1 is a block diagram showing a configuration of a remote palpation support system according to a first embodiment.

FIG. 1 is a block diagram showing a configuration of a remote palpation support system according to a first embodiment. The remote palpation support system 1 according to the first embodiment includes an information processing device for patient 10 and a information processing device for doctor 20. The information processing device for patient 10 and the information processing device for doctor 20 are communicably connected with each other via a communication network 100. The information processing device for patient 10 is installed in a patient's house or a care center, for example. The information processing device for doctor 20 is installed in a hospital or a clinic, for example. Configurations of those information processing devices will be described below.

First, a configuration of the information processing device for patient 10 is described. As shown in FIG. 1, the information processing device for patient 10 includes reception part 11, transmission part 12, input interface 13, display part 14, and control part 15.

The reception part 11 receives various kinds of data from the information processing device for doctor 20 via the communication network 100. The transmission part 12 transmits various kinds of data generated at the control part 15 to the information processing device for doctor 20 via the communication network 100.

The input interface 13 receives various kinds of instructions from a patient or a caregiver. The input interface 13 may include a keyboard, a mouse device, or a touch panel, for example. The input interface 13 transmits an output signal corresponding to an inputted instruction to the control part 15.

The display part 14 displays a variety of images relating to palpation, in which a portion of a patient's body that needs a diagnosis is touched. For example, the display part 14 is operated by a doctor to display an image showing a portion of a patient's body on which palpation is performed or a palpation method instructed through the information processing device for doctor 20.

The display part 14 includes display interface part and a display device. The display interface part converts data representing a displayed image (display information) to a video signal. The display signal is supplied to the display device. The display device displays the video signal representing the object to be displayed. The display device may include one or more displays that may be arbitrarily used. Examples of displays used in the display device include cathode ray tube (CRT) display, liquid crystal display (LCD), organic electro luminescence display (OELD), light emitting diode (LED) display, and plasma display.

As hardware resources, the control part 15 includes a processor such as a central processing unit (CPU), a micro processing unit (MPU), or a graphics processing unit (GPU), and a memory such as a read only memory (ROM) or a random access memory (RAM). The control part 15 performs a data generating function 151 based on a program stored in a ROM.

The data generating function 151 is an example of a data generator that generates palpation data and position data based on a measurement result of a tactile sensor 30. The tactile sensor 30 is attached to a palpating person, or examiner, who is a patient or a caregiver. When the examiner touches the portion that needs a diagnosis, a pressure is generated. The tactile sensor 30 is an example of a pressure measurer that measures the pressure generated in the palpation. The tactile sensor 30 includes a piezoelectric device that may sense low frequency pressure oscillations (equal to or less than 200 Hz) and to convert the pressure oscillations to electrical signals. Based on such electrical signals, the data generating function 151 generates the palpation data.

The tactile sensor 30 also includes a transmitter, which transmits an identification signal including a sensor ID for identifying the tactile sensor 30. The identification signal is received by the reception part 11. The intensity and the direction of the identification signal vary depending on the location of the tactile sensor 30 or the location of the portion that needs a diagnosis or examined portion. Therefore, the data generating function 151 generates examination position data indicating the position of the examined portion based on the intensity and the direction of the received identification signal.

A display control function 152 controls the display operation of the display part 14. Furthermore, the display control function 152 generates image data displayed by the display part 14.

A configuration of the information processing device for doctor 20 will now be described. As shown in FIG. 1, the information processing device for doctor 20 includes reception part 21, transmission part 22, input interface 23, display part 24, storage part 25, and control part 26.

The reception part 21 is an example of a palpation data acquiring part that acquires various kinds of data such as palpation data from the information processing device for patient 10 via the communication network 100. The transmission part 22 transmits various kinds of data such as instructions of a doctor relating the palpation to the information processing device for patient 10 via the communication network 100.

The input interface 23 receives various kinds of instructions from the doctor. Like the input interface 13, the input interface 23 may include a keyboard, a mouse device, or a touch panel, for example. The input interface 23 transmits an output signal corresponding to an inputted instruction to the control part 26.

The display part 24 is an example of a diagnosis support information output part that outputs various kinds of diagnosis support information relating to the palpation. For example, the display part 24 displays an image of data relating to the palpation transmitted from the information processing device for patient 10. Like the display part 14, the display part 24 includes display interface part and a display device. The display interface part converts data representing a displayed image (display information) to a video signal. The display signal is supplied to display device. The display device displays the video signal representing the object to be displayed. The display device may include one or more displays that may be arbitrarily used. Examples of displays used in the display device include CRT display, liquid crystal display, organic EL display, LED display, and plasma display.

The storage part 25 stores data such as data required for position adjustment between the patient side and the doctor side, data transmitted from the information processing device for patient 10, and image data displayed on the display part 24.

Like the control part 15, the control part 26 includes a processor and a memory as hardware resources. The control part 26 performs a data processing function 261, a display control function 262, and a palpation instruction function 263 based on a program stored in the memory.

The data processing function 261 is an example of a palpation method determining part that determines the palpation method performed by the examiner by processing the data stored in the storage part 25. Specific contents of the data processing performed by the data processing function 261 will be described later. The display control function 262 controls the display operation of the display part 24. The display control function 262 also generates image data displayed by the display part 24. The palpation instruction function 263 controls the display part 24 to display various instructions regarding the palpation relating to the portion that needs a diagnosis and the palpation method, and transmits such instructions to the information processing device for patient 10.

The operation of the remote palpation support system 1 will now be described with reference to the accompanying drawings.

Figure 2:
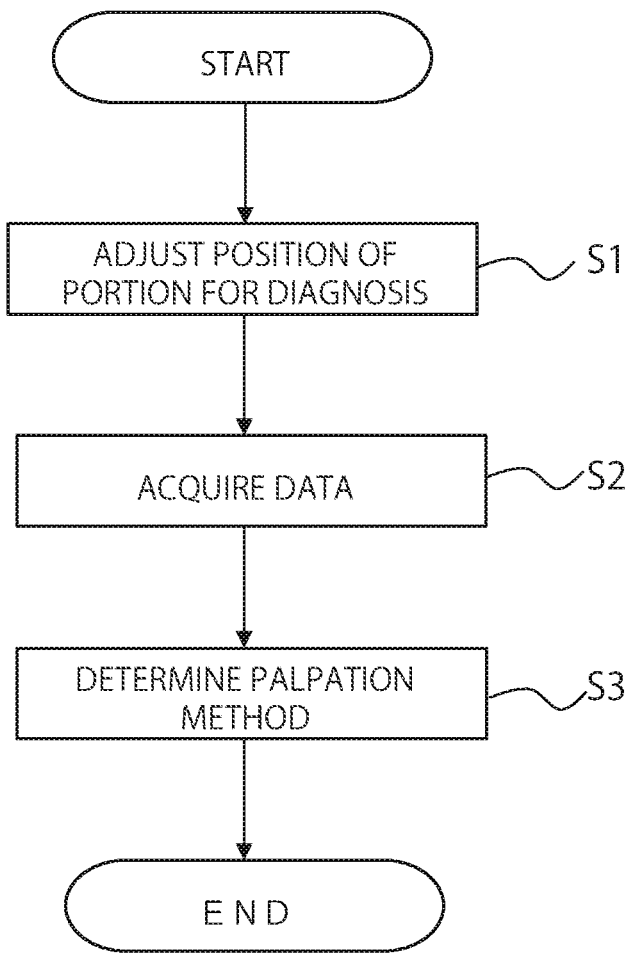
FIG. 2 is a flow chart showing an operation process of the remote palpation support system 1 according to the first embodiment.

FIG. 2 is a flow chart showing an operation process of the remote palpation support system 1 according to the first embodiment. As shown in FIG. 2, the remote palpation support system 1 according to the first embodiment first adjusts the position of the portion that needs a diagnosis by the palpation between a position coordinate system (x, y, z) on the patient side and a position coordinate system (a, b, c) on the doctor side (step S1). The remote palpation support system 1 then acquires palpation data of the portion that needs a diagnosis based on a result of measurement performed by the tactile sensor 30 (step S2). Finally, the remote palpation support system 1 determines the palpation method based on the palpation data (step S3). Each of the aforementioned steps will be described below with reference to the drawings.

Figure 3:
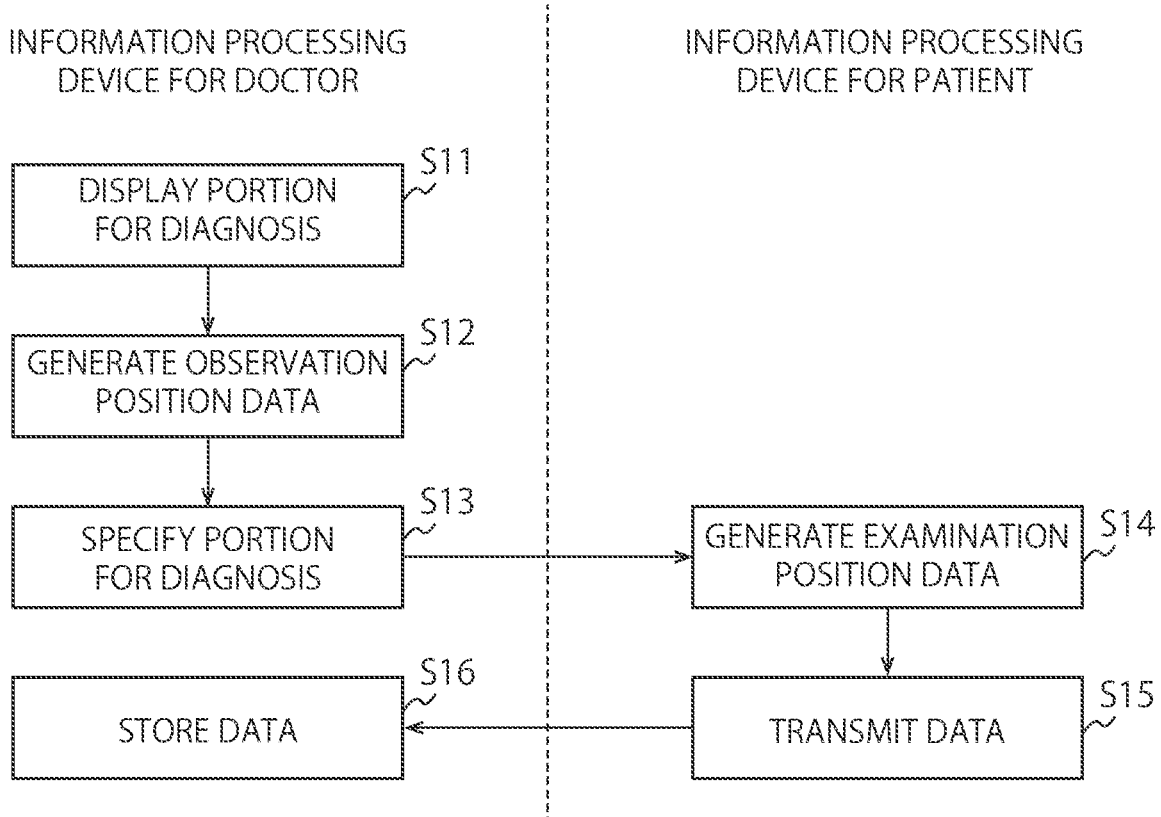
FIG. 3 is a sequence diagram showing the process of a position adjustment step.

FIG. 3 is a sequence diagram showing the process of the position adjustment step (step S1). In the position adjustment step, first the palpation instruction function 263 of the control part 26 in the information processing device for doctor 20 instructs the display control function 262 to display the portion that needs a diagnosis (step S11). The display control function 262 controls the display part 24 to display the portion that needs a diagnosis specified by the palpation instruction function 263.

Figures 4, 5:
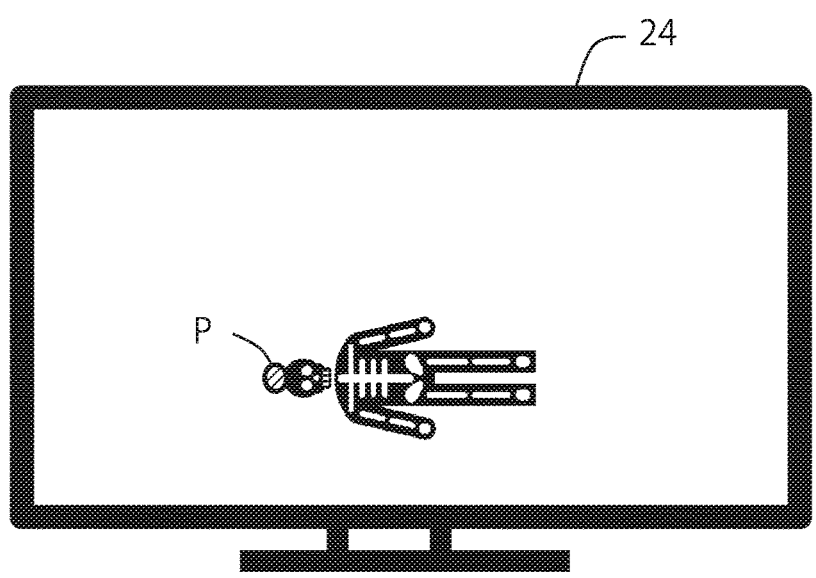
FIG. 4 shows an example of an image specifying a portion that needs a diagnosis.
FIG. 5 is a diagram showing an example of an adjustment database stored in storage part.

FIG. 4 shows an example of the image specifying the portion that needs a diagnosis. FIG. 4 shows that the display part 24 of the information processing device for doctor 20 displays an image in which the top part of the head is shown as the portion P that needs a diagnosis. In this case, the doctor touches the top part of his/her own head. A transmitter (not shown) is attached to a hand of the doctor, and a signal sent from the transmitter is received by the reception part 21 and inputted to the data processing function 261 of the control part 26.

The intensity and the direction of the received signal vary depending on the position of the transmitter. Therefore, the data processing function 261 generates observation position data indicating the portion touched by the doctor based on the intensity and the direction of the received signal (step S12). The observation position data specifies the position of the portion touched by the doctor in the position coordinate system (a, b, c) on the doctor side.

Subsequently, the transmission part 22 is controlled by the palpation instruction function 263 to transmit an instruction to specify the portion that needs a diagnosis to the information processing device for patient 10 via the communication network 100 (step S13). In the information processing device for patient 10, this instruction is received by the reception part 11 and inputted to the control part 15.

In the control part 15, the display control function 152 controls the display part 14 to display an image, which, like the image shown in FIG. 4, indicates the portion that needs a diagnosis specified by the palpation instruction function 263. If video communications may be possible between the information processing device for patient 10 and the information processing device for doctor 20, the transmission part 22 may transmit video data, in which the doctor orally specifies the portion that needs a diagnosis, to the information processing device for patient 10.

When the image indicating the portion that needs a diagnosis is displayed on the display part 14, the examiner touches the actual portion that needs a diagnosis with the tactile sensor 30 attached to his/her hand. The tactile sensor 30 then transmits an identification signal, which is received by the reception part 11 and inputted to the control part 15. The data generating function 151 of the control part 15 generates the examination position data indicating the position of the portion that needs a diagnosis based on the intensity and the direction of the identification signal (step S14). In the examination position data, the position of the portion that needs a diagnosis touched by the palpating person or examiner is specified in the position coordinate system (x, y, z) on the patient side.

Subsequently, the transmission part 12 transmits the examination position data to the information processing device for doctor 20 via the communication network 100 (step S15). The examination position data is received by the reception part 21 and stored in the storage part 25 in the information processing device for doctor 20 (step S16). Step S11 to step S16 are repeated until the examination position data and the observation position data of all portions to be examined are obtained.

FIG. 5 is a diagram showing an example of an adjustment database stored in the storage part 25. In the adjustment database shown in FIG. 5, the position of each portion is expressed as examination position data specified in the position coordinate system (x, y, z) on the patient side and observation position data specified in the position coordinate system (a, b, c) on the doctor side, the position data on the patient side and the position data on the doctor side being associated with each other. In each of the position coordinate systems, the position of the head is set as the reference position. It is possible to adjust the positions of the portions to be examined on the doctor side and the patient side based on the adjustment database. It is not necessary to obtain the examination position data and the observation position data for all the portions to be examined. For example, the examination position data and the observation position data may be obtained for only the head portion and the toe portion, and the positions of the other portions to be examined may be calculated by the ratios in the position data.

The data acquisition step (step S2) will then be described.

Figure 6:
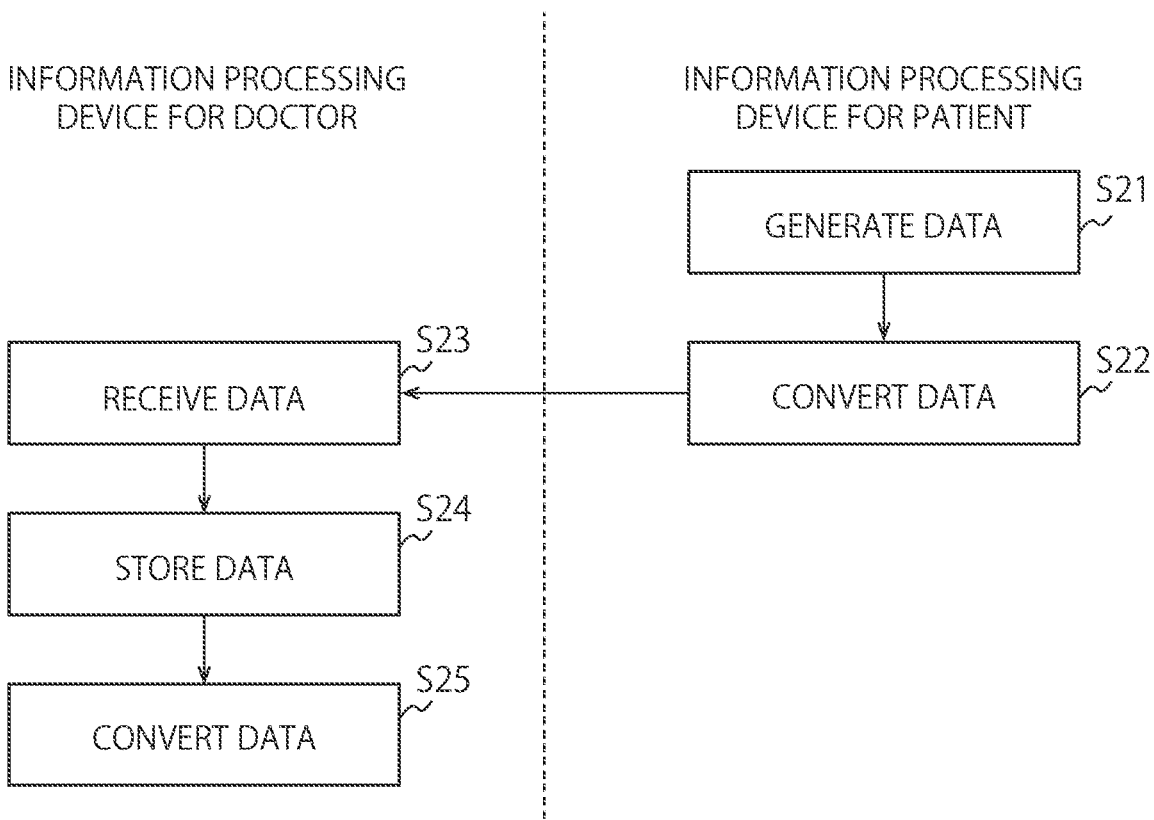
FIG. 6 is a sequence diagram showing the process of a data acquisition step.

FIG. 6 is a sequence diagram showing the process of the data acquisition step. In the data acquisition step, first, the data generating function 151 of the control part 15 included in the information processing device for patient 10 generates the palpation data and the examination position data (step S21). The following explains step S21 in detail.

Figure 7:
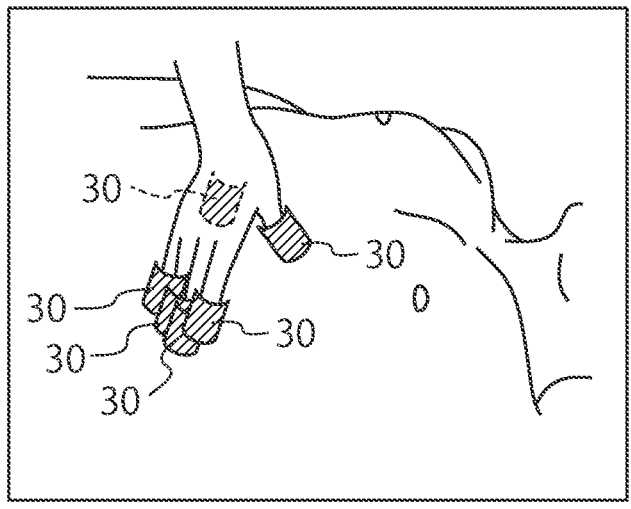
FIG. 7 illustrates an example of palpation method.
Figure 8:
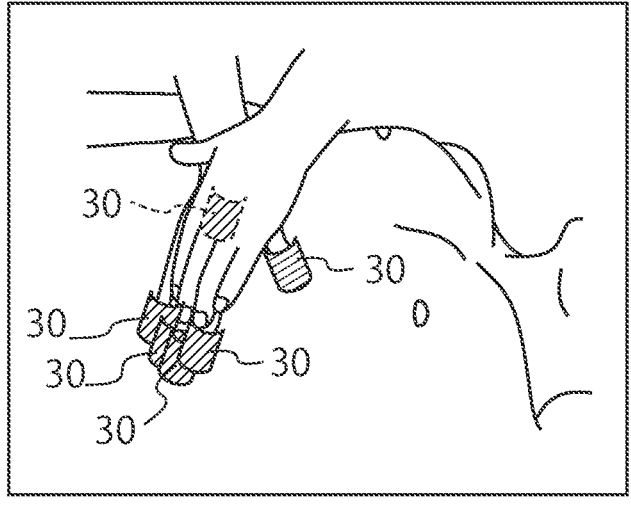
FIG. 8 illustrates another example of palpation method.

FIG. 7 illustrates an example of the palpation method. FIG. 8 illustrates another example of the palpation method. As shown in FIGS. 7 and 8, palpation is performed with a plurality of tactile sensors 30 attached to a hand of the examiner. The tactile sensors 30 are attached to the five fingers and the palm of the examiner, for example. The examiner touches the portion to be examined by a palpation method specified by the doctor in the data acquisition step or the aforementioned position adjustment step. If the portion to be examined is an abdomen portion, for example, the palpation method may be selected from two methods, superficial palpation and deep palpation.

As shown in FIG. 7, superficial palpation is a palpation method in which the examiner touches the abdomen of the patient lightly so as to sense, at the hand, the lift-up of the abdominal wall during the patient's respiration. As shown in FIG. 8, deep palpation is a palpation method in which the examiner uses the hand with the tactile sensors 30 only to sense the abdomen, and the other hand to push the hand with the tactile sensors 30 so as to apply pressure to the abdomen.

During the superficial palpation or the deep palpation, the identification signal from each of the tactile sensors 30 and the pressure value measured by each of the tactile sensors 30 are received by the reception part 11 and inputted to the data generating function 151. The data generating function 151 generates the palpation data based on the received pressure values.

Figure 9:
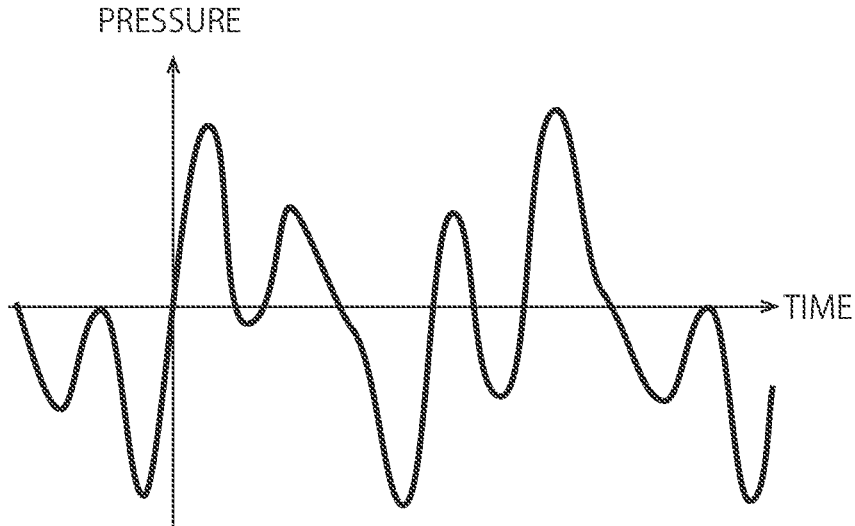
FIG. 9 is a waveform diagram illustrating an example of palpation data.

FIG. 9 is a waveform diagram illustrating an example of the palpation data. In FIG. 9, the horizontal axis represents time and the vertical axis represents pressure measured by the tactile sensors 30. The palpation data indicates the pressure applied to the examined portion of the patient.

The data generating function 151 also generates the examination position data based on the intensity and the direction of the received identification signal. This ends step S21. Subsequently, as shown in FIG. 6, the transmission part 12 transmits the palpation data and the examination position data generated by the data generating function 151 to the information processing device for doctor 20 at the same time (step S22).

FIG. 10 illustrates an example of the configuration of the transmitted data. As shown in FIG. 10, the palpation data and the examination position data are simultaneously transmitted with the sensor ID of each tactile sensor 30 being used as a header. The sensor ID is included in the identification signal transmitted from each tactile sensor 30. The palpation data and the examination position data from each tactile sensor 30 may be identified by the sensor ID.

The palpation data and the examination position data transmitted from the information processing device for patient 10 are received by the reception part 21 of the information processing device for doctor 20 (step S23), and stored in the storage part 25 (step S24). The storage part 25 stores time-series data in which the sensor ID, the examination position data, and the palpation data are stored in association with the measured time.

Subsequently, the data processing function 261 of the control part 26 generates converted data by frequency-converting the palpation data (step S25). At step S25, the data processing function 261 generates the converted data by Fourier converting the palpation data. In the converted data, the frequency (Hz) is associated with the power spectrum density (nm²/Hz). The converted data is stored in the storage part 25 in association with the palpation data.

Step S21 to step S25 are repeated until the palpation data is sufficiently acquired. Whether the amount of the palpation data is sufficient is determined by the data processing function 261. A method of determining whether the palpation data is sufficient will be described below with reference to FIG. 11.

Figure 11:
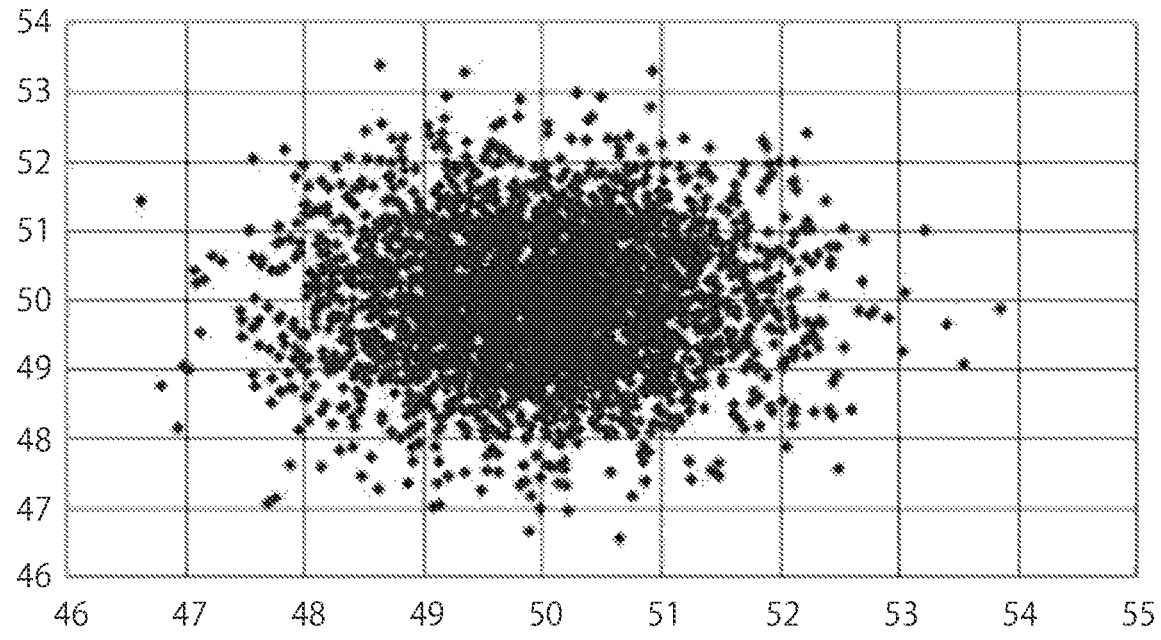
FIG. 11 is a distribution diagram on which palpation data is plotted.

FIG. 11 is a distribution diagram on which the palpation data is plotted. In the distribution diagram shown in FIG. 11, the palpation data is plotted on surface coordinates around the examined portion. In the surface coordinates, either the position coordinate system (x, y, z) on the patient side or the position coordinate system (a, b, c) on the doctor side may be used. If the position coordinate system (a, b, c) on the doctor side is used, the examination position data is converted using the adjustment database shown in FIG. 5.

The data processing function 261 forms the distribution diagram shown in FIG. 11 and calculates the density of the palpation data based on the distribution diagram. When the calculated density becomes greater than a reference value, the data processing function 261 determines that the amount of the palpation data is appropriate. When the acquisition of the palpation data is finished, the data processing function 261 determines the palpation method.

The palpation method determination step (step S3) will be described below.

Figure 12:
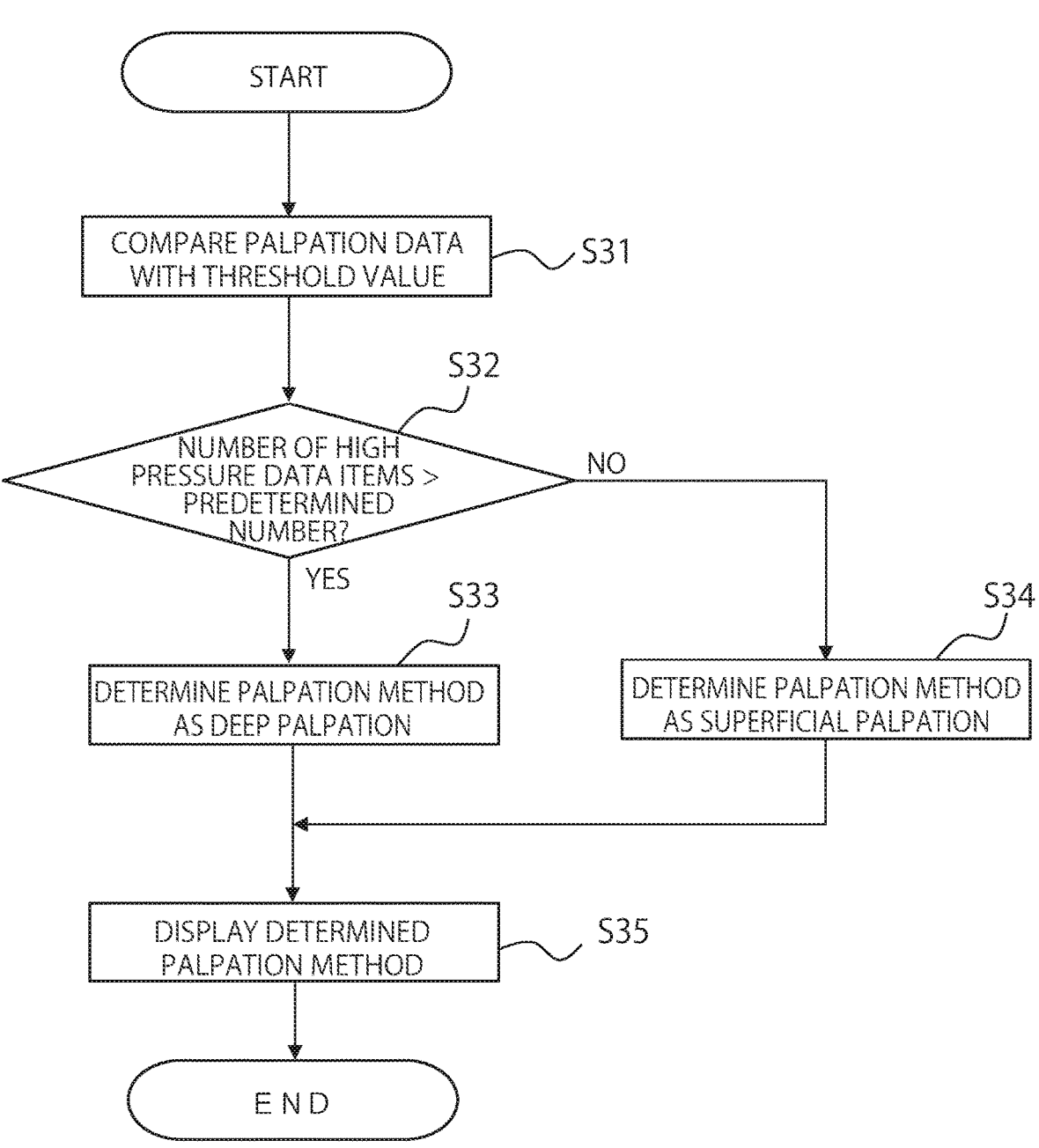
FIG. 12 is a flow chart showing the process of a palpation method determination step.

FIG. 12 is a flow chart showing the process of the palpation method determination step. In the palpation method determination step, first the data processing function 261 compares the values of the palpation data (in other words, pressure data) concurrently measured by the tactile sensors 30 and stored in the storage part 25 with a threshold value (step S31). The data processing function 261 counts the number of palpation data values which are greater than the threshold value, in other words high pressure data values.

Subsequently, the data processing function 261 determines whether the number of high pressure data values counted is larger than a predetermined number (step S32). In the deep palpation shown in FIG. 8, in which the portion that needs a diagnosis is pressed with two hands, it is likely that high pressure data values are obtained. On the other hand, in the superficial palpation shown in FIG. 7, in which the portion that needs a diagnosis is lightly touched with one hand, it is unlikely that high pressure data values are obtained.

Therefore, if the amount of high pressure data is larger than the predetermined number, the data processing function 261 determines that the palpation method is the deep palpation method (step S33). One the other hand, if the amount of high pressure data is equal to or less than the predetermined number, the data processing function 261 determines that the palpation method is the superficial palpation method (step S34).

Subsequently, the display control function 262 displays the palpation method determined by the data processing function 261 (step S35).

Figure 13:
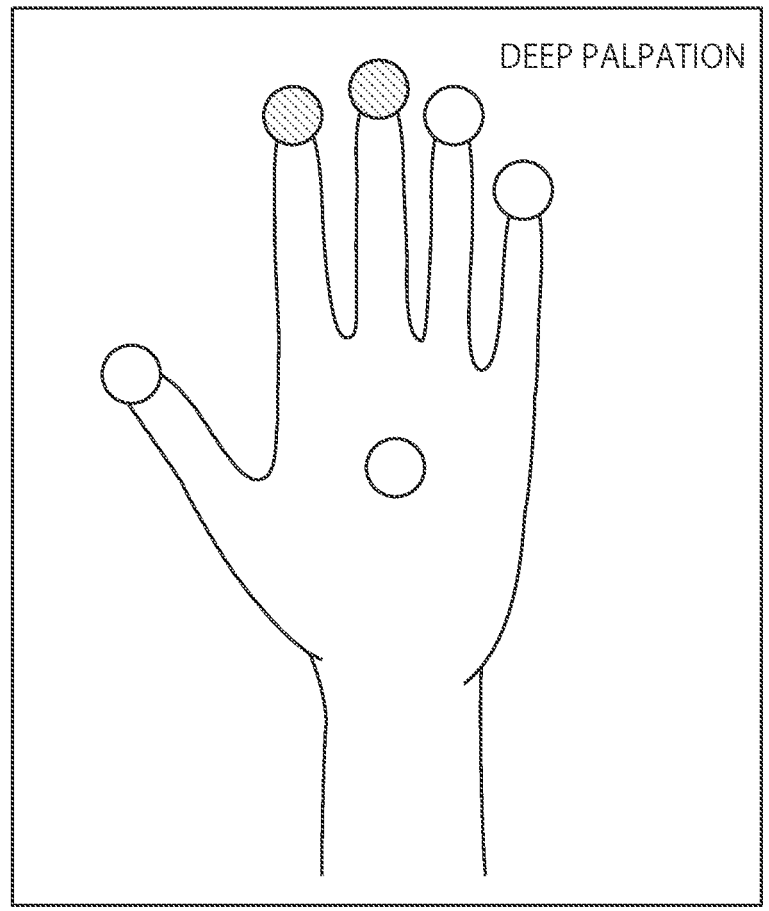
FIG. 13 illustrates an example of an image displayed to indicate a deep palpation method.

FIG. 13 illustrates an example of an image displayed to indicate the deep palpation method. In FIG. 13, the portions where the tactile sensors 30 determined to provide high pressure data values are attached, specifically the index finger and the middle finger, are highlighted and emphasized as compared to other portions. If the measurement results of the tactile sensors 30 are displayed in association with the portions where they are attached, as shown in FIG. 13, the doctor may confirm that the palpation method requested on the doctor side is performed on the patient side. The palpation method may be determined by using data obtained by frequency-converting the palpation data. In this case, the data processing function 261 determines the palpation method by, for example, using a comparison result of the power spectrum density values in the same frequency region of the tactile sensor 30.

When the position adjustment step (step S1), the data acquisition step (step S2), and the palpation method determination step (step S3) are performed for all of the portions to be examined, the doctor checks the palpation result using the remote palpation support system 1. The check method performed by the doctor will be described below.

If the doctor touches a portion for observation with a hand, to which the transmitter used in the position adjustment step is attached, the data processing function 261 generates the observation position data based on a signal from the transmitter.

The data processing function 261 then determines the portion that needs a diagnosis corresponding to the observation position data based on the adjustment database (see FIG. 5) stored in the storage part 25. Thereafter, the display control function 262 reads the converted data of the portion that needs a diagnosis determined by the data processing function 261 from the storage part 25 and controls the display part 24 to display the converted data.

Figure 14:
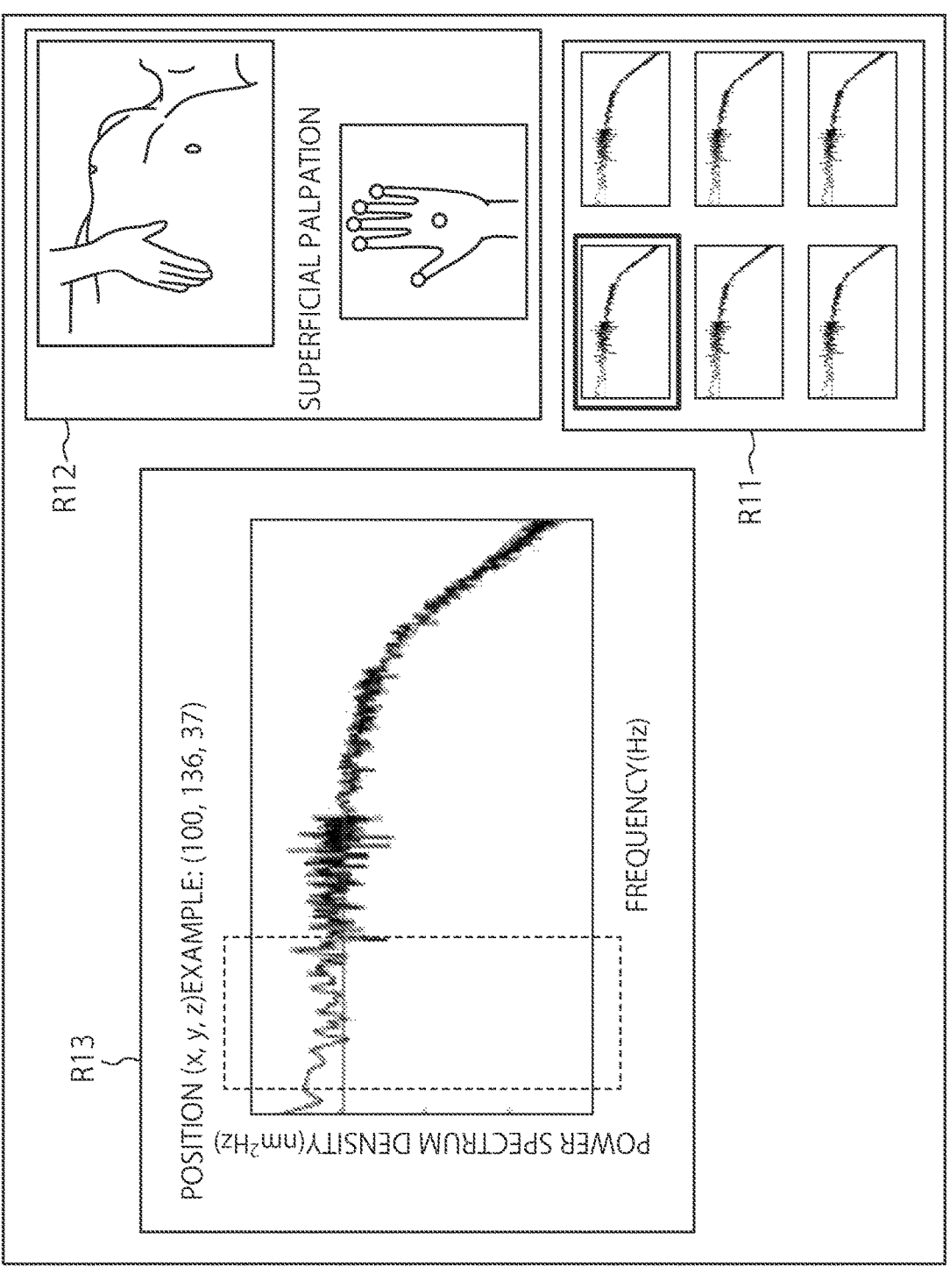
FIG. 14 illustrates an example of displayed image indicating the palpation result requested by the doctor.
Figure 15:
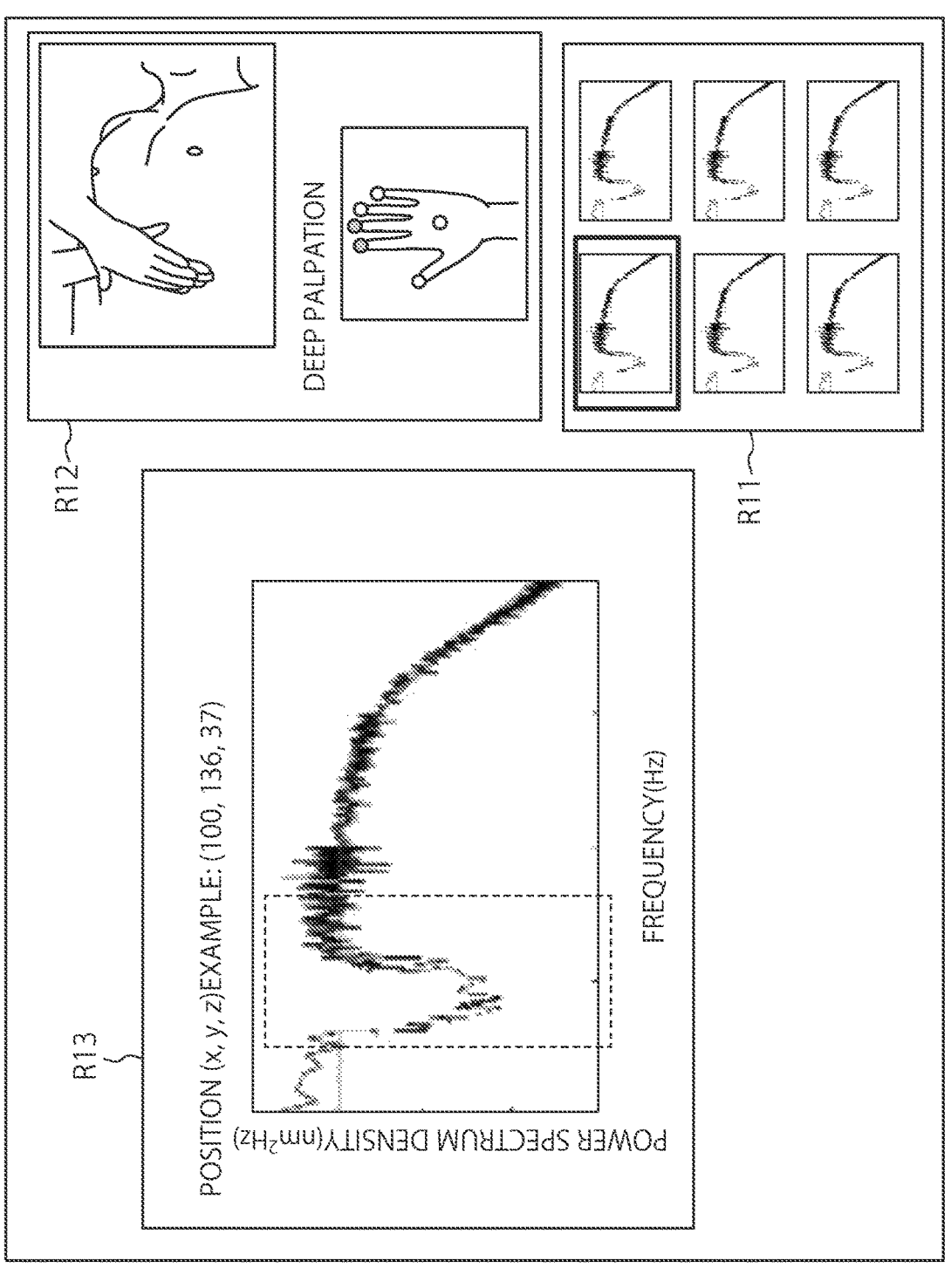
FIG. 15 illustrates another example of displayed image indicating the palpation result requested by the doctor.

FIG. 14 illustrates an example of the displayed image indicating the palpation result requested by the doctor. FIG. 15 illustrates another example of the displayed image indicating the palpation result requested by the doctor.

The displayed images in FIGS. 14 and 15 are examples of diagnosis support information obtained based on the palpation data. The displayed image in each of FIGS. 14 and 15 includes an image region R11, an image region R12, and an image region R13. In the image region R11, waveform diagrams of the converted data corresponding to the tactile sensors 30 are displayed. In the image region R12, an image showing the palpation method determined by the data processing function 261 is displayed. This region in FIG. 14 shows the superficial palpation, and this region in FIG. 15 shows the deep palpation. In the image region R13, an enlarged view of one of the waveform diagrams shown in the image region R11, selected by the doctor through the input interface 23, is displayed.

In the waveform diagram representing the converted data displayed in the image region R13 of FIG. 15, the power spectrum density decreases in a low-frequency region. Based on this, the doctor may point out the possibility that an edema may be present in the examined portion. In the first embodiment, the palpation data corresponding to the converted data displayed in the image region R13 may be reproduced on the doctor side. Specifically, the tactile sensors 30 may also be attached to the doctor, and the electrical signal corresponding to the palpation data may also be inputted to those tactile sensors 30. In this case, the piezoelectric devices included in the tactile sensors 30 attached to the doctor convert the electrical signal to pressure oscillations. As a result, the doctor may feel how palpation is performed. Therefore, the diagnosis accuracy may be improved.

As described above, according to the first embodiment, the data processing function 261 determines the palpation method. Therefore, it may be possible to determine whether the palpation data is acquired by the palpation method requested by the doctor. As the palpation data corresponding to the palpation method is acquired in this manner, the characteristics of the portion that needs a diagnosis may be understood more easily. This improves the reliability of the palpation data, and helps perform a high quality diagnosis using remote palpation.

Furthermore, in the first embodiment, the position of the portion that needs a diagnosis is adjusted between the doctor side and the patient side, the palpation method is determined based on the palpation data, and the converted data needed for the diagnosis is displayed. Therefore, the doctor may make diagnosis by palpation without watching how the portion that needs a diagnosis is touched. As a result, a portion where the patient does not want the doctor to see or touch can be examined with a palpation method.

Since the data acquired during the palpation is stored in the storage part 25, the way how the palpation is performed may be replicated. As a result, the doctor may provide an opinion or a diagnosis after a lapse of time.

Second Embodiment

Figure 16:
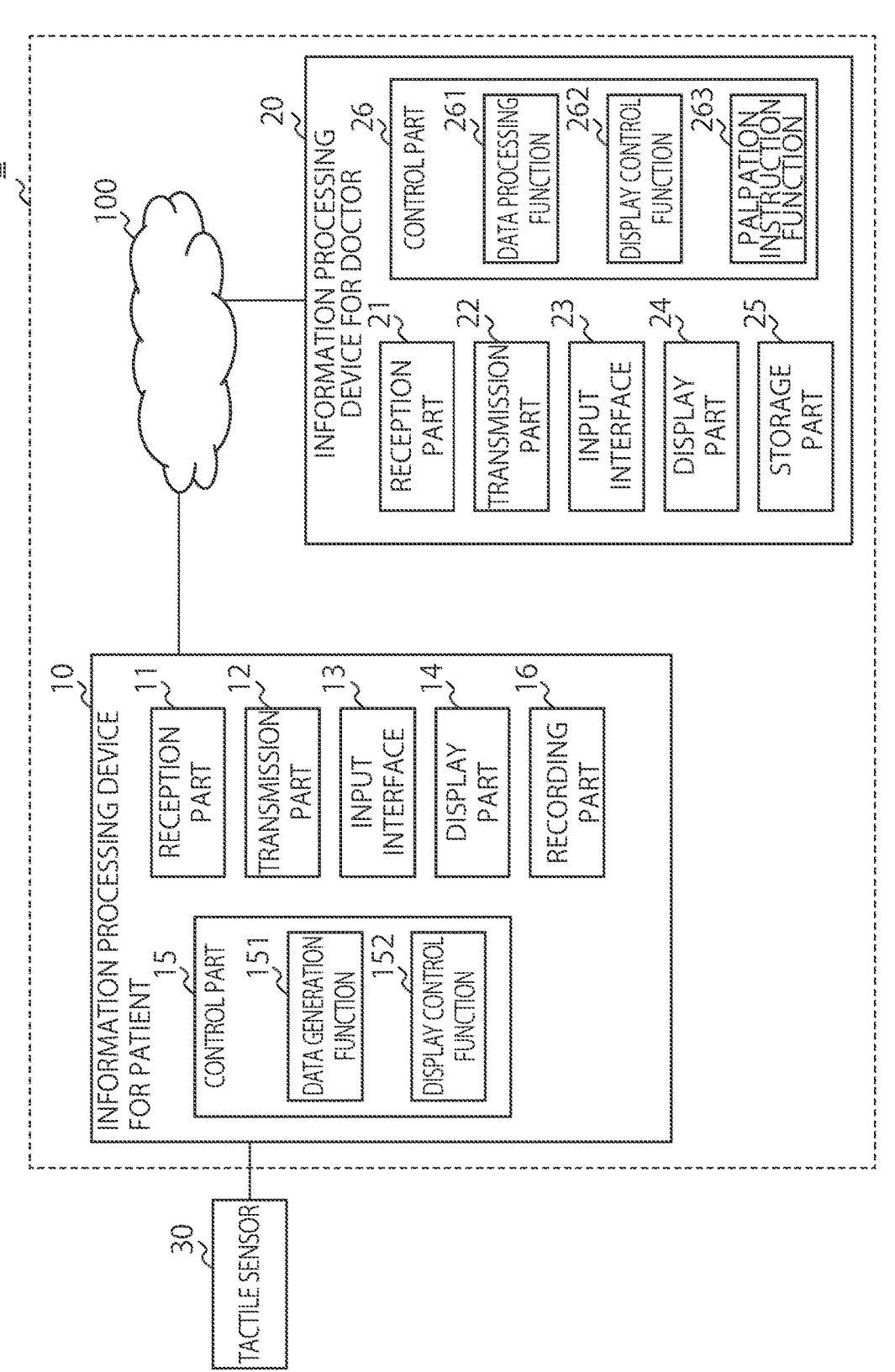
FIG. 16 is a block diagram showing a configuration of a remote palpation support system according to a second embodiment.

FIG. 16 is a block diagram showing a configuration of a remote palpation support system according to a second embodiment. In FIG. 16, elements common to those of the remote palpation support system 1 according to the first embodiment described above have the same reference numerals, and are not described in detail.

As shown in FIG. 16, the remote palpation support system 2 according to the second embodiment additionally has recording part 16 included in the information processing device for patient 10. The recording part 16 records voices or sounds of the patient during the palpation, and outputs the voices or sounds to the control part 15. The data generating function 151 of the control part 15 generates recorded data.

Figure 17:
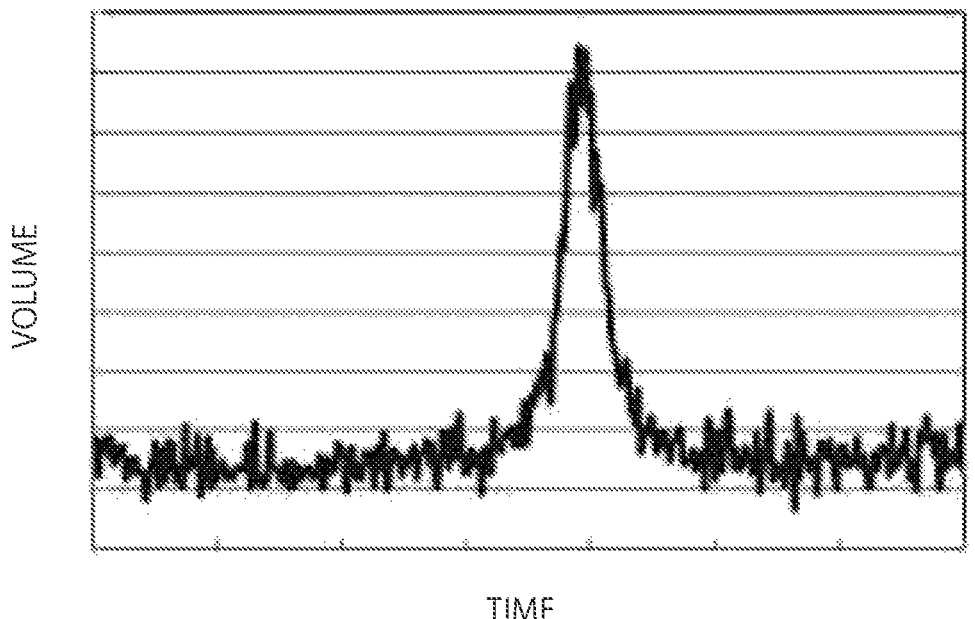
FIG. 17 is a waveform diagram showing an example of recorded data.

FIG. 17 is a waveform diagram showing an example of the recorded data. As shown in FIG. 17, the recorded data indicates changes in time of the volume of voices or sounds recorded by the recording part 16. When the data generating function 151 generates the recorded data, the transmission part 12 transmits the recorded data to the information processing device for doctor 20 at the same time as the palpation data and the examination position data.

In the information processing device for doctor 20, the recorded data is received by the reception part 21, and stored in the storage part 25 together with the palpation data and the examination position data. The data processing function 261 then detects voices or sounds made from pressure pain based on the volume of the recorded data. When a patient feels pain during palpation, the volume of the voices of the patient becomes higher than usual. Therefore, if the volume level of a portion of the recorded data is higher than a reference level, the data processing function 261 determines the portion as being associated with pressure pain. The method of determining the pressure pain is not limited. For example, the data processing function 261 may search for a keyword such as "ouch" in the recorded data, and determines that a portion including the keyword of the recorded data includes pressure pain voice or sound.

Figure 18:
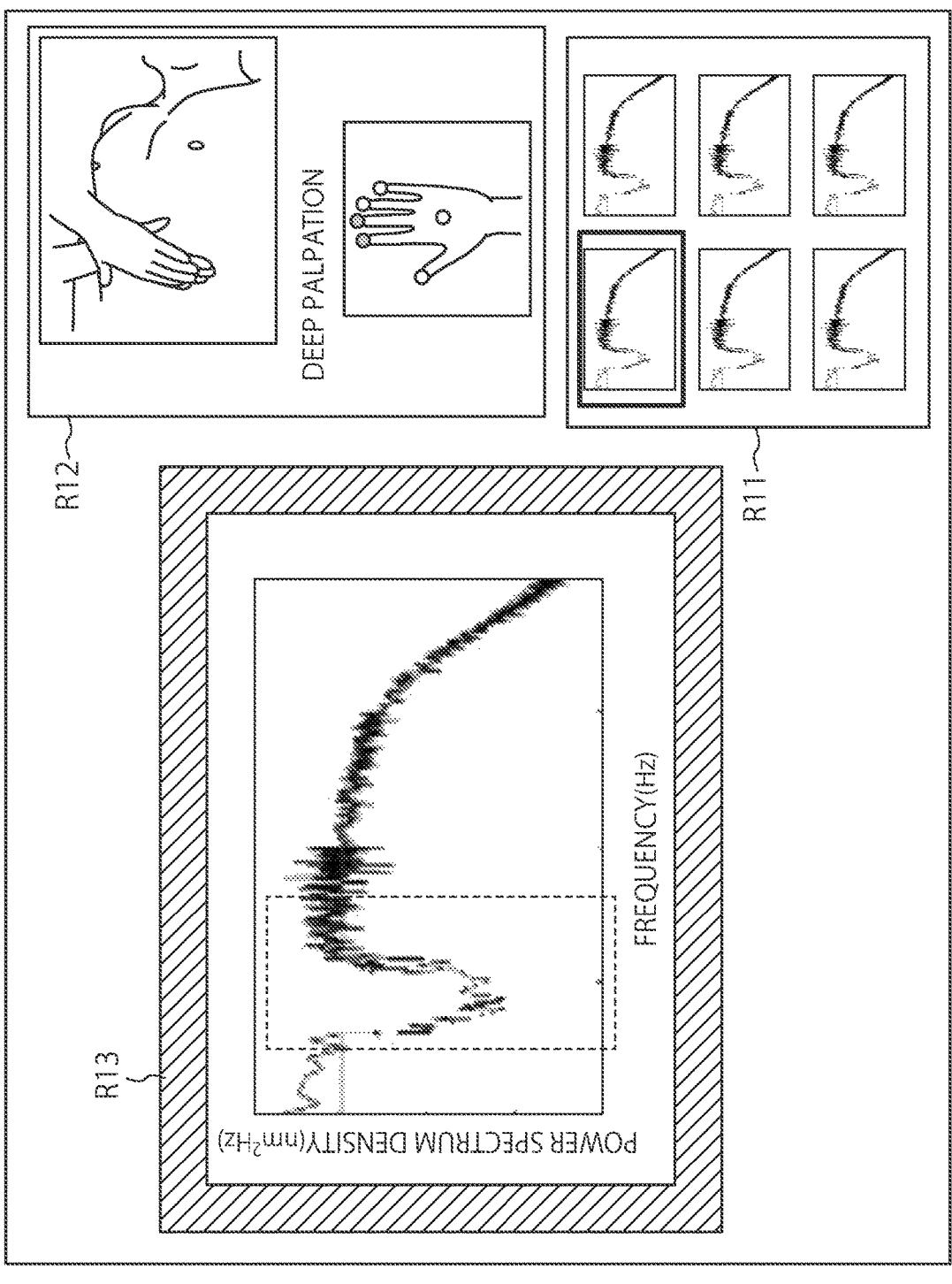
FIG. 18 is a diagram in which converted data including recorded pressure pain voices or sounds is highlighted.

The storage part 25 may also store a pressure pain flag indicating the presence of pressure pain voices or sounds. The display part 24 may highlight the converted data including the recorded pressure pain voices or sounds, as shown in FIG. 18. For example, the highlighting may be performed by changing the color of the frame of the image region R13 (to red, for example) or causing the frame to flash to draw attention of the doctor.

As described above, according to the second embodiment, the data processing function 261 determines the palpation method as in the case of the first embodiment. Therefore, it is possible to determine whether the palpation data is acquired by a palpation method requested by the doctor. This improves the reliability of the palpation data, and helps perform a high quality diagnosis using remote palpation.

Furthermore, in the second embodiment, the converted data obtained when the patient feels pressure pain during palpation is highlighted. This makes it easier to narrow the area to be examined of the patient. As a result, the examination time may be shortened.

Third Embodiment

Figure 19:
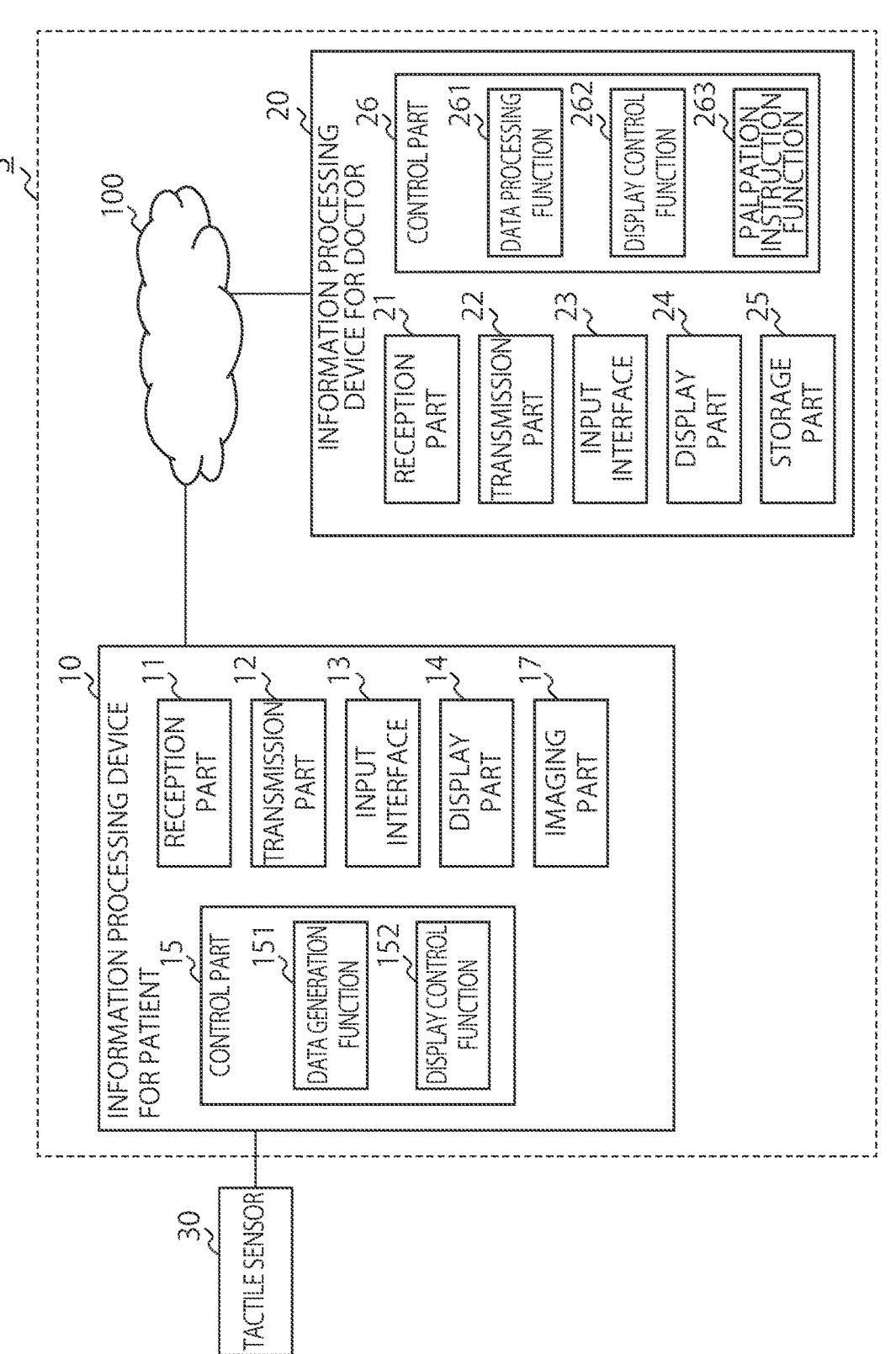
FIG. 19 is a block diagram showing a configuration of a remote palpation support system according to a third embodiment.

FIG. 19 is a block diagram showing a configuration of a remote palpation support system according to a third embodiment. In FIG. 19, elements common to those of the remote palpation support system 1 according to the first embodiment described above have the same reference numerals, and are not described in detail.

As shown in FIG. 19, the remote palpation support system 3 according to the third embodiment has imaging part 17 included in the information processing device for patient 10. The imaging part 17 includes a camera, for example, and takes an image showing how the palpation proceeds. The imaging part 17 then outputs the image to the control part 15. The data generating function 151 of the control part 15 generates image data showing the contents of the image taken by the imaging part 17.

After the data generating function 151 generates the image data, the transmission part 12 transmits the image data to the information processing device for doctor 20 together with the palpation data and the examination position data. The information processing device for doctor 20 receives the image data at the reception part 21, and stores the image data in the storage part 25 together with the palpation data and the examination position data.

Thereafter, the data processing function 261 analyzes the image data to determine the palpation method. As shown in FIGS. 7 and 8, the use of hands pressing the portion that needs a diagnosis differs between the superficial palpation and the deep palpation. The data processing function 261 uses not only the analysis result of the palpation data but also the analysis result of the image data to determine the palpation method. The display part 24 displays the image data so that the doctor may check by the eyes whether the palpation performed on the patient side meets the request made on the doctor side.

As described above, according to the third embodiment, not only the palpation data but also the image data representing how the palpation proceeds is used to determine the palpation method. As a result, the palpation method may be determined more accurately. This further improves the quality of the remote palpation diagnosis.

In the first to third embodiments described above, the information processing device for patient 10 and the information processing device for doctor 20 are constituent elements of the systems. This may mean that the information processing device for patient 10 and the information processing device for doctor 20 constitute a palpation support device that acquires palpation data and outputs a palpation method determined based on the acquired palpation data as a piece of diagnosis support information. Furthermore, in the first to third embodiments, palpation is performed on the patient at a location that is far away from the doctor's place. However, the doctor may be in company with the patient, but the patient or a caregiver may serve as an examiner to touch the patient. In this case, the information processing device for patient 10 and the information processing device for doctor 20 may not be connected with each other via the communication network 400, but may be integrally formed as a palpation support device. Specifically, the palpation support device acquires palpation data based on a plurality of pressure values generated during the palpation performed by the examiner, and provides the doctor with diagnosis support information based on the acquired palpation data. In the diagnosis support information, the palpation method is determined, for example. Therefore, the accuracy of the palpation diagnosis may be improved.

While certain embodiments have been described, these embodiments have been presented by the way of example only, and are not intended to limit the scope of the inventions. Indeed, the novel methods and systems described herein may be embodied in a variety of other forms. Furthermore, various omissions, substitutions, changes, and combinations of the embodiments may be made without departing from the spirit of the inventions. The accompanying claims and their equivalents are intended to cover such embodiments and modifications as would fail within the scope and spirit of the inventions.

The invention claimed is:

1. A palpation support system, comprising:
a first information processing device for a patient, the first information processing device including a palpation data acquiring part configured to acquire a plurality of palpation data based on a plurality of pressure values measured by a plurality of tactile sensors attached to at least two or more fingers of an examiner, and a transmitter configured to transmit the plurality of palpation data;
a second information processing device for a doctor, the second information processing device including a receiver configured to receive the plurality of palpation data, and second processing circuitry configured to determine a palpation method performed by the examiner among a plurality of palpation methods, based on the plurality of palpation data; and
a display configured to display information indicating the palpation method and a schematic diagram of a hand, wherein the schematic diagram displays a location where the tactile sensors are attached and identification information corresponding to the plurality of pressure values detected by the plurality of tactile sensors.

2. The palpation support system according to claim 1, wherein the first information processing device includes first processing circuitry configured to generate the palpation data based on the plurality of pressure values measured by the plurality of tactile sensors.

3. The palpation support system according to claim 2, wherein the second processing circuitry is further configured to determine the palpation method based on a comparison between the palpation data measured by each of the tactile sensors and a threshold value.

4. The palpation support system according to claim 2, wherein the second processing circuitry is further configured to generate converted data by frequency-converting the palpation data, and wherein a diagnosis support information output part displays the converted data as a piece of the diagnosis support information.

5. The palpation support system according to claim 4, further comprising a recorder configured to record voices or sounds during palpation, wherein the first processing circuitry is further configured to generate recorded data based on the voices or sounds recorded by the recorder, wherein the second processing circuitry is further configured to detect pressure pain voices or sounds based on a volume level of the recorded data, and wherein the diagnosis support information output part highlights the converted data corresponding to the recorded data in which the pressure pain voices or sounds are detected.

6. The palpation support system according to claim 4, further comprising a memory configured to store the palpation data and examination position data in association with each other, wherein the examination position data indicates a position of an examined portion of the palpation measured when the examiner performs the palpation method.

7. The palpation support system according to claim 6, wherein the memory stores the examination position data and observation position data in association with each other, wherein the examination position data is measured by a first position coordinate system on a side of the patient, wherein the observation position data is measured by a second position coordinate system on a side of the doctor and indicates a position of the examined portion, and wherein the second processing circuitry is further configured to determine the examined portion based on the observation position data, and read, from the memory, the converted data corresponding to the examined portion.

8. The palpation support system according to claim 6, wherein the second processing circuitry is further configured to determine whether a number of the palpation data is enough based on a distribution diagram on which the palpation data is plotted based on the examination position data.

9. The palpation support system according to claim 2, further comprising an imager configured to make an image of palpation, wherein the first processing circuitry is further configured to generate image data indicating contents of the image made by the imager.

10. The palpation support system according to claim 1, wherein the display is further configured to highlight an attached portion that indicates a high pressure data value greater than a threshold value.

11. A palpation support method, comprising:
acquiring, by an information processing device for a patient, a plurality of palpation data based on a plurality of pressure values measured by a plurality of tactile sensors attached to at least two or more fingers of an examiner;
transmitting the plurality of palpation data from the information processing device for the patient;
receiving the plurality of palpation data by an information processing device for a doctor;
determining a palpation method performed by the examiner among a plurality of palpation methods, based on the plurality of palpation data received by the information processing device for the doctor; and displaying, on a display, information indicating the palpation method and a schematic diagram of a hand, wherein the schematic diagram displays a location where the tactile sensors are attached and identification information corresponding to the plurality of pressure values detected by the plurality of tactile sensors.

\* \* \* \* \*